(12) United States Patent
Vaysse-Ludot et al.

(10) Patent No.: US 8,859,763 B1
(45) Date of Patent: Oct. 14, 2014

(54) PROCESS FOR THE SYNTHESIS OF 3,4-DIMETHOXYBICYCLO[4.2.0]OCTA-1,3,5-TRIENE-7-CARBONITRILE, AND APPLICATION IN THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Lucile Vaysse-Ludot, St-Wandrille-Rancon (FR); Alexandre Le Flohic, Fauville en Caux (FR); Michel Vaultier, Chateaugiron (FR); Mathieu Pucheault, Camblanes et Meynac (FR); Thomas Kaminski, Rennes (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 14/277,151

(22) Filed: May 14, 2014

(30) Foreign Application Priority Data

May 17, 2013 (FR) ...................................... 13 54504

(51) Int. Cl.
C07D 223/16 (2006.01)
C07C 253/00 (2006.01)
(52) U.S. Cl.
CPC ............ C07D 223/16 (2013.01); C07C 253/00 (2013.01)
USPC ......................................... 540/523; 558/308

(58) Field of Classification Search
USPC .......................................... 540/523; 558/308
See application file for complete search history.

(56) References Cited

FOREIGN PATENT DOCUMENTS

WO WO 2011 138825 11/2011

OTHER PUBLICATIONS

French Preliminary Search Reportfor FR 1354505 of Jan. 21, 2014.
Harold Hart, et al., The Journal of Organic Chemistry, vol. 31, No. 7. pp. 2244-1150, Jul. 1, 1966.
Tetsuji Kametani, et al., Journal of the Chemical Society, Perkin Transactions 1, pp. 1712-1714, Jan. 1, 1974.
van Leusen, D., et al., Organic Reactions, vol. 57, pp. 417-489 and 659-679, Apr. 15, 2004.

*Primary Examiner* — Kristin Vajda
(74) *Attorney, Agent, or Firm* — Hueschen and Sage

(57) ABSTRACT

Process for the synthesis of the compound of formula (I):

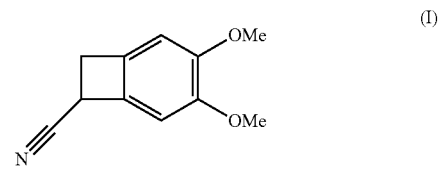

Application in the synthesis of ivabradine, addition salts thereof with a pharmaceutically acceptable acid and hydrates thereof.

17 Claims, No Drawings

PROCESS FOR THE SYNTHESIS OF 3,4-DIMETHOXYBICYCLO[4.2.0]OCTA-1,3,5-TRIENE-7-CARBONITRILE, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of 3,4-dimethoxybicyclo-[4.2.0]octa-1,3,5-triene-7-carbonitrile of formula (I):

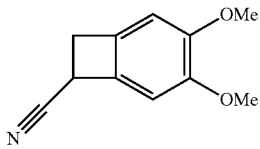

and to the application thereof in the synthesis of ivabradine and addition salts thereof with a pharmaceutically acceptable acid.

The compound of formula (I) obtained by the process of the invention is useful in the synthesis of ivabradine of formula (II):

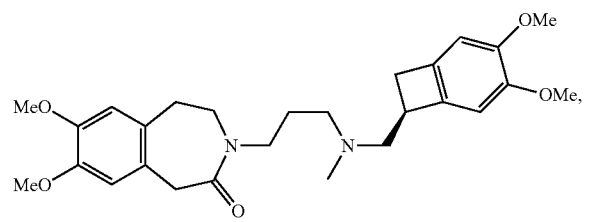

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the preparation of ivabradine starting from 3,4-dimethoxybicyclo[4.2.0]octa-1,3,5-triene-7-carbonitrile of formula (I):

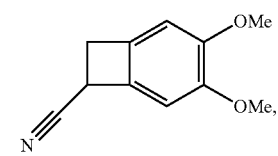

which is converted into the compound of formula (III):

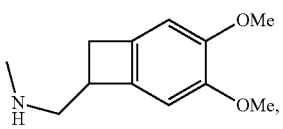

which is resolved to yield the compound of formula (IV):

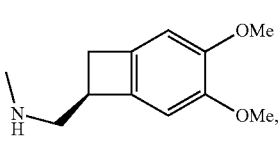

which is reacted with the compound of formula (V):

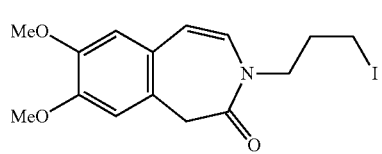

to yield the compound of formula (VI):

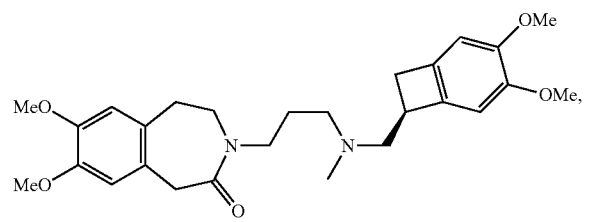

the catalytic hydrogenation of which yields ivabradine, which is then converted into its hydrochloride.

In view of the industrial value of ivabradine and salts thereof, it is imperative to find an effective process allowing the compound of formula (I) to be obtained in a good yield.

The patent application WO 2011/138 625 describes the preparation of the compound of formula (I) by intramolecular cyclisation of 3-(2-bromo-4,5-dimethoxyphenyl)propane-nitrile in the presence of lithium diethylamide or lithium diisopropylamide.

The present invention relates to a process for the synthesis of the compound of formula (I):

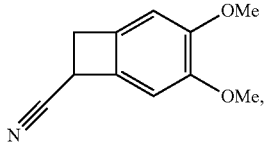

characterised in that the compound of formula (VII):

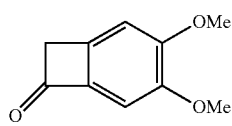

is subjected to the action of 1-(isocyanomethylsulphonyl)-4-methylbenzene (TosMIC) in the presence of a base in an organic solvent or mixture of organic solvents to yield the compound of formula (I).

The amount of 1-(isocyanomethylsulphonyl)-4-methylbenzene preferably used to carry out the conversion of the compound of formula (VII) to form the compound of formula (I) is from 2 to 5 equivalents.

Among the bases that may be used to carry out the conversion of the compound of formula (VII) to form the compound of formula (I), there may be mentioned, without implying any limitation, organic bases of the alkoxide type such as potassium tert-butoxide, sodium tert-butoxide, potassium ethoxide, sodium ethoxide, potassium methoxide and sodium methoxide.

The base preferably used to carry out the conversion of the compound of formula (VII) to form the compound of formula (I) is potassium tert-butoxide.

Among the organic solvents that may be used to carry out the conversion of the compound of formula (VII) to form the compound of formula (I), there may be mentioned, without implying any limitation, alcohols such as methanol, ethanol, isopropanol, tert-butanol, tetrahydrofuran, ethylene glycol and dimethyl sulphoxide.

The organic solvent used to carry out the conversion of the compound of formula (VII) to form the compound of formula (I) may also be composed of a mixture of two solvents from among the afore-mentioned organic solvents.

The solvent preferably used to carry out the conversion of the compound of formula (VII) to form the compound of formula (I) is a mixture of tetrahydrofuran and methanol.

The conversion of the compound of formula (VII) to form the compound of formula (I) is preferably carried out at a temperature from −20° C. to 50° C.

The present invention relates also to a process for the synthesis of the compound of formula (I) starting from the compound of formula (VII), characterised in that said compound of formula (VII) is prepared starting from the compound of formula (VIII):

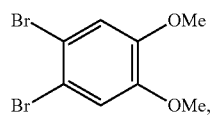

which is converted into a compound of formula (IX):

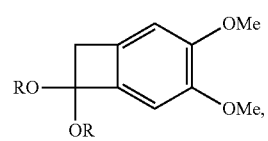

wherein R represents a $(C_1-C_4)$alkyl group,
in the presence of a 1,1-dialkoxyethene, wherein the alkoxy groups have from 1 to 4 carbon atoms, and an organometallic compound in an organic solvent,
which is converted into the compound of formula (VII):

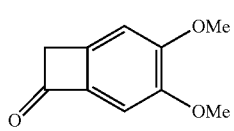

by a hydrolysis reaction,
which is converted into the product of formula (I):

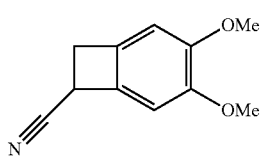

in accordance with the process described hereinbefore.

The 1,1-dialkoxyethene preferably used to carry out the conversion of the compound of formula (VIII) to form the compound of formula (IX) is 1,1-diethoxyethene.

The amount of 1,1-diethoxyethene preferably used to carry out the conversion of the compound of formula (VIII) to form the compound of formula (IX) is from 0.8 to 5 equivalents.

Among the organometallic compounds that may be used to carry out the conversion of the compound of formula (VIII) to form the compound of formula (IX), there may be mentioned, without implying any limitation, n-butyllithium, s-butyllithium, t-butyllithium, phenyllithium and isopropylmagnesium chloride.

The organometallic compound preferably used to carry out the conversion of the compound of formula (VIII) to form the compound of formula (IX) is n-butyllithium.

The amount of n-butyllithium preferably used to carry out the conversion of the compound of formula (VIII) to form the compound of formula (IX) is from 1 to 3 equivalents.

Among the organic solvents that may be used to carry out the conversion of the compound of formula (VIII) to form the compound of formula (IX), there may be mentioned, without implying any limitation, toluene, tetrahydrofuran, dichloromethane and chlorobenzene.

The solvent preferably used to carry out the conversion of the compound of formula (VIII) to form the compound of formula (IX) is toluene.

The conversion of the compound of formula (VIII) to form the compound of formula (IX) is preferably carried out at a temperature from −20° C. to 30° C.

The hydrolysis reaction performed on the compound of formula (IX) to form the compound of formula (VII) may be carried out in an organoaqueous acidic medium composed of a mixture:
- of an organic solvent such as tetrahydrofuran, ethyl acetate, toluene or dichloromethane, and
- an aqueous acid such as hydrochloric acid (1N to 12N) in excess.

The following Examples illustrate the invention.

The melting points were measured using a capillary melting point apparatus of the Buchi B-545 Melting point type.

The NMR spectra are recorded on a Bruker apparatus at 400 MHz for the proton spectra and at 100 MHz for the carbon spectra.

The chemical shifts (δ) are expressed in terms of ppm (internal standard: TMS).

The following abbreviations are used to quantify the peaks: singlet (s), doublet (d), doublet of doublets (dd), triplet (t), quadruplet (q), multiplet (m).

LIST OF ABBREVIATIONS USED m.p.: melting point
THF: tetrahydrofuran
TosMIC: 1-(isocyanomethylsulphonyl)-4-methylbenzene Preparation A: 1,2-dibromo-4,5-dimethoxybenzene 16.16 g of 1,2-dimethoxybenzene (117 mmol) are stirred at 0° C. in $CCl_4$ (120 mL). 13.2 mL of dibromine (2.2 eq; 257.4 mmol; 41.13 g) dissolved in $CCl_4$ (25 mL) are added dropwise (30 min) whilst monitoring the temperature (0-5° C.) [Fit an outlet which bubbles into a solution of $Na_2CO_3$ in order to neutralise the hydrobromic acid which forms]. After stirring for 2 hours at 0° C., the reaction mixture is then poured onto a mixture of water+ice, and the organic phase is washed with aqueous 10% $NaHSO_3$ solution and then with aqueous 10% NaOH solution. After evaporation and drying, 33.42 g of a white solid corresponding to the title product are obtained.
Yield=97%
m.p. 92-93° C.
$^1$H NMR ($CDCl_3$): δ=7.06 (s; 2H); 3.86 (s; 6H).
$^{13}$C NMR ($CDCl_3$): δ=148.8; 115.9; 114.7; 56.2.

Preparation B: 1,1-diethoxyethene

The equipment set-up is as follows: a 50-ml flask provided with a distillation set (column ~20 cm; condenser ~20 cm, distillation thermometer). 20 g of 2-bromo-1,1-diethoxyethane (101.25 mmol) are quickly added (1 minute) to potassium tert-butoxide (102 mmol; 11.4 g) cooled in an ice bath. Very dense white smoke is formed. When the reaction is complete (5-10 minutes), the reaction mixture is heated to 120-130° C. (hot-plate reading), and the tert-butanol generated during the reaction is distilled off at atmospheric pressure. When all the tert-butanol has been distilled off, a water-jet pump is connected to the distillation set. In this way, the expected product is distilled off in vacuo in a few seconds. 8.5 g of a colourless liquid containing traces of tert-butanol are obtained.
Yield=72%
$^1$H NMR ($CDCl_3$): δ=3.78 (q; 4H); 3.03 (s; 2H); 1.25 (t; 6H).

Example 1

7,7-diethoxy-3,4-dimethoxybicyclo[4.2.0]octa-1,3,5-triene 2.55 g of 1,2-dibromo-4,5-dimethoxybenzene (8.62 mmol; 2 eq) and 500 mg of 1,1-diethoxyethene (4.31 mmol; 1 eq) in 25 mL of toluene are stirred at 0° C. under argon. 3.5 mL of n-butyllithium (2.5M in hexane, 8.62 mmol; 2 eq) are added dropwise at 0° C. When the addition is complete, the reaction mixture is stirred for 22 hours at ambient temperature. The reaction mixture is then hydrolysed and extracted 3 times with ethyl acetate. The organic phases are dried and evaporated, and the crude product is purified by column chromatography over silica gel (eluant: heptane/ethyl acetate 90/10). There are obtained 333 mg of a yellow oil which crystallises at ambient temperature.
Yield=31%
$^1$H NMR ($CDCl_3$): δ=6.86 (s; 1H); 6.79 (s; 1H); 3.84 (s; 6H); 3.72 (q; 4H); 3.30 (s; 2H); 1.25 (t; 6H).

Example 2

3,4-dimethoxybicyclo[4.2.0]octa-1,3,5-trien-7-one 7,7-Diethoxy-3,4-dimethoxybicyclo[4.2.0]octa-1,3,5-triene (1.76 g, 6.98 mmol) is stirred in a mixture of THF/water (6/1) at ambient temperature. 815 mg of an aqueous 11N HCl solution (1.1 eq, 7.7 mmol) are then added. The reaction mixture is stirred for 2 hours ambient temperature. Water is added to facilitate two extractions with ethyl acetate (2×30 mL). The organic phases are dried over $MgSO_4$ and then subjected to drying. There are obtained 1.01 g of the title product in the form of a grey powder.
Yield=81%
$^1$H NMR ($CDCl_3$): 7.02 (s; 2H); 6.82 (s; 2H); 3.99 (s; 3H); 3.87 (s; 5H).
$^{13}$C NMR ($CDCl_3$): 185.8; 155.9; 151.4; 146.2; 138.7; 105.6; 102.3; 56.4; 56.1; 51.0.
m.p.=146° C.

Example 3

3,4-dimethoxybicyclo[4.2.0]octa-1,3,5-triene-7-carbonitrile

A solution of TosMIC (0.98 g, 4.98 mmol, 2.3 eq) in THF (3 mL) is poured, over 20 minutes, into a solution of potassium tert-butoxide (1.22 g; 10.9 mmol; 5 eq) in THF (7.5 mL) stirred at 0° C. under nitrogen. Then 200 µL of methanol are added to the mixture and stirring is maintained for 30 minutes at 0° C. In parallel, 3,4-dimethoxybicyclo[4.2.0]octa-1,3,5-trien-7-one (0.39 g, 2.17 mmol, 1 eq), lithium bromide (0.19 g, 2.17 mmol, 1 eq) and THF (2.5 mL) are transferred into a second three-necked flask. After cooling to 0° C. under nitrogen, the solution of TosMIC and potassium tert-butoxide is transferred to the reaction mixture. After returning to ambient temperature, the solution is heated to 40° C. and stirred for 16 hours at that temperature. The mixture is then hydrolysed with a solution of 11N HCl (0.7 mL, 7.73 mmol) in water (2 mL). After evaporating off the THF under reduced pressure, the product is extracted with 5 mL of dichloromethane. The organic phase is washed twice with 2×5 mL of water before being dried. The crude product is purified by column chromatography over silica gel using the binary mixture methylcyclohexane/ethyl acetate 75/25 to obtain the title product in the form of a cream-coloured powder.

Yield=54%

$^1$H NMR (CDCl$_3$): 6.76 (s; 1H); 6.68 (s; 1H); 4.14 (m; 1H); 3.83 (s; 6H); 3.59-3.41 (m; 2H).

$^{13}$C NMR (CDCl$_3$): 151.4; 150.4; 134.2; 129.7; 119.9; 106.9; 106.1; 56.2; 35.5; 22.6.

Example 4

3,4-dimethoxy-N-methylbicyclo[4.2.0]octa-1,3,5-trien-7-amine

Based on EP 0 534 859

Step 1: 3,4-dimethoxybicyclo[4.2.0]octa-1,3,5-trien-7-amine hydrochloride 312 mL of a molar solution of borane complexed with THF are added dropwise, and whilst stirring at ambient temperature, to a solution of 25 g of 3,4-dimethoxybicyclo[4.2.0]octa-1,3,5-triene-7-carbonitrile in 250 mL of THF and left in contact for 12 hours; 200 mL of ethanol are then added and stirring is carried out for 1 hour. 100 mL of 3.3N ethereal HCl are added dropwise. 27.7 g of the expected product are obtained.

Yield=90% m.p.=205° C.

Step 2: ethyl (3,4-dimethoxybicyclo[4.2.0]octa-1,3,5-trien-7-yl)carbamate 1.5 mL of ethyl chloroformate are poured into a suspension of 3.4 g of the compound obtained in Step 1 in 4.5 mL of triethylamine and 50 mL of dichloromethane and left overnight, whilst stiffing at ambient temperature; washing with water and with 1N hydrochloric acid is then carried out. Drying is carried out and the solvent is evaporated off to dryness. 3.2 g of an oil corresponding to the expected product are obtained.

Yield=80%

Step 3: 3,4-dimethoxy-N-methylbicyclo[4.2.0]octa-1,3,5-trien-7-amine 3.2 g of the compound obtained in Step 2 dissolved in 30 mL of THF are added to a suspension of 0.9 g of LiAlH$_4$ in 20 mL of THF. Refluxing is carried out for 1 hour 30 minutes, then hydrolysing using 0.6 ml of water and 0.5 mL of 20% sodium hydroxide solution and, finally, 2.3 mL of water. The mineral salts are then filtered off, rinsed with THF and then the filtrate obtained is evaporated to dryness. 2.3 g of the expected compound are obtained.

Yield=92%

Example 5

(7S)-3,4-dimethoxy-N-methylbicyclo[4.2.0]octa-1,3,5-trien-7-amine

Based on EP 0 534 859

The amine obtained in Example 4 is reacted with an equimolar amount of (d) camphorsulphonic acid in ethanol. After evaporating off the solvent in vacuo, the salt is recrystallised first from ethyl acetate and then from acetonitrile until the target enantiomer is obtained with an optical purity of more than 99% (evaluated by HPLC on a Chiralcel® OD column).

Example 6

3-{3-[{[(7S)-3,4-dimethoxybicyclo[4.2.0]octa-1,3,5-trien-7-yl]methyl}-(methyl)amino]propyl}-7,8-dimethoxy-1,3-dihydro-2H-3-benzazepin-2-one Based on EP 0 534 859

A solution of the (d) camphorsulphonate salt obtained in Example 5 in ethyl acetate is brought to basic pH using sodium hydroxide and then the organic phase is separated off, washed, dried over Na$_2$SO$_4$ and evaporated.

A mixture composed of 5.6 g of potassium carbonate, 2.2 g of the above amine in 100 mL of acetone and 4 g of 3-(3-iodopropyl)-7,8-dimethoxy-1,3-dihydro-2H-3-benzazepin-2-one is then refluxed for 18 hours.

The solvent is evaporated off in vacuo, and the residue is taken up in ethyl acetate and then extracted with 3N hydrochloric acid.

The aqueous phase separated off is brought to basic pH using sodium hydroxide and is then extracted with ethyl acetate. After washing until neutral and drying over MgSO$_4$, evaporation in vacuo is carried out to obtain 4.5 g of an oil which is purified on a silica column using a mixture of dichloromethane/methanol (90/10) as eluant.

Yield=64%

Example 7

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one Based on EP 0 534 859

5 g of the compound obtained in Example 6 in 50 mL of glacial acetic acid are hydrogenated in a Parr apparatus under a hydrogen pressure of 4.9 bar at ambient temperature for 24 hours in the presence of 1 g of palladium hydroxide 10%. The catalyst is filtered off, the solvent is evaporated off, and then the dry residue is taken up in water and ethyl acetate. The organic phase is dried over anhydrous magnesium sulphate, concentration in vacuo is carried out and then the residue is purified on a silica column using a mixture of dichloromethane/methanol (95/5) as eluant. After recrystallisation from ethyl acetate, 2 g of the expected compound are obtained.

Yield=40% m.p.=101-103° C.

The invention claimed is:

1. A process for the synthesis of a compound of formula (I):

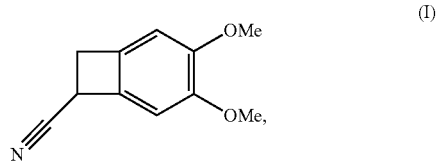 [SMILES: COc1cc2c(cc1OC)C(C#N)C2]

(I)

wherein a compound of formula (VII):

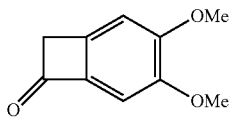

is subjected to the action of 1-(isocyanomethylsulphonyl)-4-methylbenzene (TosMIC) in the presence of a base in an organic solvent to yield the compound of formula (I).

2. The process according to claim 1, wherein the amount of 1-(isocyanomethylsulphonyl)-4-methylbenzene used to carry out the conversion of the compound of formula (VII) to form the compound of formula (I) is from 2 to 5 equivalents.

3. The process according to claim 1, wherein the base used to carry out the conversion of the compound of formula (VII) to form the compound of formula (I) is selected from the group consisting of potassium tert-butoxide, sodium tert-butoxide, potassium ethoxide, sodium ethoxide, potassium methoxide and sodium methoxide.

4. The process according to claim 3, wherein the base used to carry out the conversion of the compound of formula (VII) to form the compound of formula (I) is potassium tert-butoxide.

5. The process according to claim 1, wherein the organic solvent used to carry out the conversion of the compound of formula (VII) to form the compound of formula (I) is selected from the group consisting of methanol, ethanol, isopropanol, tert-butanol, tetrahydrofuran, ethylene glycol, dimethyl sulphoxide, and a mixture of two from among those solvents.

6. The process according to claim 5, wherein the organic solvent used to carry out the conversion of the compound of formula (VII) to form the compound of formula (I) is a mixture of tetrahydrofuran and methanol.

7. The process according to claim 1, wherein the conversion of the compound of formula (VII) to form the compound of formula (I) is carried out at a temperature from −20° C. to 50° C.

8. The process according to claim 1, wherein the compound of formula (VII) is prepared starting from a compound of formula (VIII):

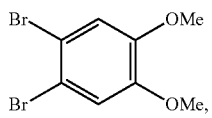

which is converted into a compound of formula (IX):

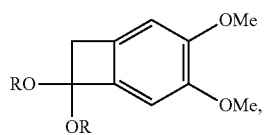

wherein R represents a $(C_1$-$C_4)$alkyl group,
in the presence of a 1,1-dialkoxyethene, wherein the alkoxy groups have from 1 to 4 carbon atoms, and an organometallic compound in an organic solvent,
which compound of formula (IX) is hydrolysed in an organoaqueous acidic medium to form the compound of formula (VII):

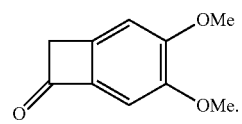

9. The process according to claim 8, wherein the 1,1-dialkoxyethene used to carry out the conversion of the compound of formula (VIII) to form the compound of formula (IX) is 1,1-diethoxyethene.

10. The process according to claim 9, wherein the amount of 1,1-diethoxyethene used to carry out the conversion of the compound of formula (VIII) to form the compound of formula (IX) is from 0.8 to 5 equivalents.

11. The process according to claim 8, wherein the organometallic compound used to carry out the conversion of the compound of formula (VIII) to form the compound of formula (IX) is selected from the group consisting of n-butyllithium, s-butyllithium, t-butyllithium, phenyllithium and isopropylmagnesium chloride.

12. The process according to claim 11, wherein the organometallic compound used to carry out the conversion of the compound of formula (VIII) to form the compound of formula (IX) is n-butyllithium.

13. The process according to claim 12, wherein the amount of n-butyllithium used to carry out the conversion of the compound of formula (VIII) to form the compound of formula (IX) is from 1 to 3 equivalents.

14. The process according to claim 8, wherein the organic solvent used to carry out the conversion of the compound of formula (VIII) to form the compound of formula (IX) is selected from the group consisting of toluene, tetrahydrofuran, dichloromethane and chlorobenzene.

15. The process according to claim 14, wherein the organic solvent used to carry out the conversion of the compound of formula (VIII) to form the compound of formula (I) is toluene.

16. The process according to claim 8, wherein the conversion of the compound of formula (VIII) to form the compound of formula (IX) is carried out at a temperature from −20° C. to 30° C.

17. A process for the synthesis of ivabradine, pharmaceutically acceptable salts thereof and hydrates thereof, wherein the compound of formula (VII) is converted into the compound of formula (I) according to the process of claim 1, and then the compound of formula (I) is converted into ivabradine.

* * * * *